United States Patent [19]

Lamshing et al.

[11] Patent Number: 5,929,274
[45] Date of Patent: Jul. 27, 1999

[54] METHOD TO REDUCE CARBOXYBENZALDEHYDE ISOMERS IN TEREPHTHALIC ACID OR ISOPHTHALIC ACID

[75] Inventors: Wiston Lamshing; Fu-Ming Lee, both of Katy, Tex.; Randi Wright Wytcherley, Belgrade, Mont.

[73] Assignee: HFM International, Inc., Houston, Tex.

[21] Appl. No.: 09/098,060

[22] Filed: Jun. 16, 1998

Related U.S. Application Data

[63] Continuation-in-part of application No. 09/074,251, May 7, 1998, and application No. 08/962,030, Oct. 31, 1997, which is a continuation-in-part of application No. 08/760,890, Dec. 6, 1996, which is a continuation-in-part of application No. 08/477,898, Jun. 7, 1995, Pat. No. 5,767,311, said application No. 09/074,251, is a division of application No. 08/477,898.

[51] Int. Cl.⁶ ................................................. C07C 51/487
[52] U.S. Cl. ........................................................... 562/487
[58] Field of Search ...................................... 562/485, 487

[56] References Cited

U.S. PATENT DOCUMENTS

| | | | |
|---|---|---|---|
| 2,636,899 | 2/1953 | Burrows et al. | 260/524 |
| 2,811,548 | 10/1957 | Ham et al. | 260/525 |
| 2,829,160 | 4/1958 | Stehman et al. | 260/525 |
| 2,833,816 | 5/1958 | Saffer et al. | 260/524 |
| 2,833,817 | 5/1958 | Saffer et al. | 260/524 |
| 2,849,483 | 8/1958 | Ham | 260/516 |
| 2,891,992 | 6/1959 | Raecks et al. | 260/515 |
| 2,905,709 | 9/1959 | Scheak et al. | 260/515 |
| 2,923,736 | 2/1960 | Maclean | 260/525 |
| 2,949,483 | 8/1960 | Ham | 260/516 |
| 3,330,863 | 7/1967 | Read et al. | 260/525 |
| 3,388,156 | 6/1968 | Sakurai et al. | 260/525 |
| 3,431,296 | 3/1969 | Ichikawa et al. | 260/525 |
| 3,465,035 | 9/1969 | Nakaguchi et al. | 260/525 |
| 3,497,552 | 2/1970 | Olsen | 260/525 |
| 3,505,398 | 4/1970 | Baldwin | 260/525 |
| 3,574,727 | 4/1971 | Taylor et al. | 260/525 |
| 3,584,039 | 6/1971 | Meyer | 260/525 |
| 3,766,257 | 10/1973 | Wimer et al. | 260/515 |
| 3,766,258 | 10/1973 | Engelbrecht et al. | 260/515 |
| 3,859,344 | 1/1975 | Shigeyasu et al. | 260/524 |
| 3,862,218 | 1/1975 | Stautzenberger | 260/525 |
| 3,887,613 | 6/1975 | Blay | 260/525 |
| 3,899,530 | 8/1975 | Syoji et al. | 260/525 |
| 3,931,305 | 1/1976 | Fisher | 260/525 |
| 3,953,502 | 4/1976 | Fassell et al. | 260/525 |
| 4,053,506 | 10/1977 | Park et al. | 260/525 |
| 4,081,464 | 3/1978 | Marsh et al. | 260/524 |
| 4,165,337 | 8/1979 | Yoshinaka et al. | 260/544 |
| 4,197,412 | 4/1980 | Kimura et al. | 562/416 |
| 4,201,871 | 5/1980 | Tanouchi et al. | 562/486 |
| 4,201,872 | 5/1980 | Kimura et al. | 562/487 |
| 4,228,299 | 10/1980 | Ferguson et al. | 560/124 |
| 4,230,882 | 10/1980 | Seko et al. | 562/416 |
| 4,245,078 | 1/1981 | Suzuki et al. | 562/412 |
| 4,260,817 | 4/1981 | Thompson et al. | 562/487 |
| 4,263,452 | 4/1981 | Komatsu et al. | 562/487 |
| 4,268,690 | 5/1981 | Komatsu et al. | 562/416 |
| 4,275,230 | 6/1981 | Donaldson | 562/486 |
| 4,281,179 | 7/1981 | Komatsu et al. | 562/416 |
| 4,286,101 | 8/1981 | Hashizume et al. | 562/487 |
| 4,297,507 | 10/1981 | Komatsu et al. | 562/416 |
| 4,314,073 | 2/1982 | Crooks | 562/416 |
| 4,317,923 | 3/1982 | Imai | 562/487 |
| 4,331,824 | 5/1982 | Ikeda et al. | 585/638 |
| 4,334,090 | 6/1982 | Donaldson | 562/480 |
| 4,340,752 | 7/1982 | List et al. | 562/485 |
| 4,345,089 | 8/1982 | Nagura et al. | 560/77 |
| 4,357,475 | 11/1982 | Hanotier et al. | 562/414 |
| 4,380,662 | 4/1983 | Hanotier et al. | 562/486 |
| 4,415,479 | 11/1983 | Puskas et al. | 502/85 |
| 4,438,279 | 3/1984 | Packer et al. | 562/416 |
| 4,447,646 | 5/1984 | Johnson et al. | 562/487 |
| 4,459,418 | 7/1984 | Greenshields | 549/370 |
| 4,467,110 | 8/1984 | Puskas et al. | 562/487 |
| 4,467,111 | 8/1984 | Puskas et al. | 562/487 |

(List continued on next page.)

FOREIGN PATENT DOCUMENTS

| | | |
|---|---|---|
| 611607 | 6/1962 | Belgium . |
| 614720 | 9/1962 | Belgium . |
| 615996 | 10/1962 | Belgium . |
| 732838 | 10/1969 | Belgium . |
| 1316914 | 2/1963 | France . |
| 1117100 | 11/1961 | Germany . |
| 818211 | 8/1959 | United Kingdom . |
| 881460 | 3/1960 | United Kingdom . |
| 908011 | 10/1962 | United Kingdom . |
| 1049720 | 11/1966 | United Kingdom . |
| 1290981 | 9/1972 | United Kingdom . |

OTHER PUBLICATIONS

Tr. Vses. Nauch.–Issled. Proekt. Inst. Monomerov (1970), 2(2), 26–32; From: Ref. Zh., Khim. 1971, Abstr. No. 1N166; V.N. Kulakov, et al.; "Purification of Aromatic Dicarboxylic Acids Obtained by Liquid–Phase Oxidation of Dialkyl Derivatives of Aromatic Hydrocarbons".

Abstract—Database WPI XP–002063355, Section Ch, Derwent Publications Ltd., London, GB; Class A41, Appl. No. 96–017160, Pat. No. JP7291896; Mitsubishi Gas Chem. Co., Inc., "Preparation of High–Purity Terephthalic Acid" (Nov. 1995).

Abstract—Database WPI XP–002063356, Section Ch, Derwent Publications Ltd., 1983 London, GB; Class A41, Appl. No. 72–77189T, Pat. No. JP47046663B; Toray Ind., Inc., "Crystallization Process for Purification of Materials Containing Trace Impurities".

*Primary Examiner*—Samuel Barts
*Attorney, Agent, or Firm*—Jenkens & Gilchrist, P.C.

[57] ABSTRACT

A method for reducing carboxybenzaldehyde isomers in crude terephthalic and/or isophthalic acids is described. Crude TPA or IPA is dissolved in N-methyl pyrrolidone and is subsequently contacted with an oxidant, such as substantially anhydrous hydrogen peroxide, to convert the carboxybenzaldehyde isomer (4-CBA or 3-CBA) to TPA or IPA under moderate temperature and pressure conditions.

42 Claims, 2 Drawing Sheets

U.S. PATENT DOCUMENTS

| | | | |
|---|---|---|---|
| 4,485,244 | 11/1984 | Fox et al. | 549/245 |
| 4,490,554 | 12/1984 | Tanaka et al. | 562/486 |
| 4,500,732 | 2/1985 | Petty-Weeks et al. | 562/486 |
| 4,537,980 | 8/1985 | Greenshields | 549/370 |
| 4,540,493 | 9/1985 | Dickerson et al. | 210/669 |
| 4,605,763 | 8/1986 | Kiefer et al. | 562/487 |
| 4,625,059 | 11/1986 | Shibano et al. | 562/600 |
| 4,626,598 | 12/1986 | Packer et al. | 562/487 |
| 4,629,715 | 12/1986 | Schroeder | 502/185 |
| 4,652,674 | 3/1987 | James et al. | 562/414 |
| 4,675,108 | 6/1987 | Dickerson et al. | 210/275 |
| 4,675,438 | 6/1987 | Schwartz et al. | 562/416 |
| 4,728,630 | 3/1988 | Schroeder et al. | 502/185 |
| 4,772,748 | 9/1988 | Hashizume et al. | 562/413 |
| 4,782,181 | 11/1988 | James | 562/487 |
| 4,791,226 | 12/1988 | Puskas et al. | 562/487 |
| 4,808,751 | 2/1989 | Schroeder et al. | 562/487 |
| 4,827,026 | 5/1989 | Brugge et al. | 562/416 |
| 4,833,269 | 5/1989 | Schroeder | 562/484 |
| 4,877,900 | 10/1989 | Tamaru et al. | 562/413 |
| 4,886,901 | 12/1989 | Holzhauer et al. | 560/77 |
| 4,892,972 | 1/1990 | Schroeder et al. | 562/487 |
| 4,933,491 | 6/1990 | Albertins et al. | 562/416 |
| 4,933,492 | 6/1990 | Schroeder et al. | 562/487 |
| 4,937,378 | 6/1990 | Schroeder | 562/487 |
| 4,939,297 | 7/1990 | Browder et al. | 562/485 |
| 4,948,921 | 8/1990 | Green et al. | 562/413 |
| 5,068,410 | 11/1991 | Tanaka et al. | 562/483 |
| 5,095,144 | 3/1992 | Sato et al. | 562/481 |
| 5,095,145 | 3/1992 | Rosen | 562/483 |
| 5,095,146 | 3/1992 | Zeitlin et al. | 562/486 |
| 5,097,066 | 3/1992 | Holzhauer et al. | 562/487 |
| 5,107,020 | 4/1992 | Reeve | 562/416 |
| 5,110,984 | 5/1992 | Janulis | 562/487 |
| 5,113,015 | 5/1992 | Palmer et al. | 562/608 |
| 5,132,450 | 7/1992 | Tanaka et al. | 562/414 |
| 5,159,109 | 10/1992 | Rosen et al. | 562/509 |
| 5,166,420 | 11/1992 | Shiraki et al. | 562/487 |
| 5,169,977 | 12/1992 | Iwane et al. | 562/417 |
| 5,175,355 | 12/1992 | Streich et al. | 562/485 |
| 5,175,358 | 12/1992 | Iwane et al. | 562/417 |
| 5,183,933 | 2/1993 | Harper et al. | 562/414 |
| 5,189,209 | 2/1993 | Ohta et al. | 562/414 |
| 5,200,557 | 4/1993 | Gee et al. | 562/486 |
| 5,254,719 | 10/1993 | Holzhauer et al. | 560/78 |
| 5,256,817 | 10/1993 | Sikkenga et al. | 562/487 |
| 5,292,934 | 3/1994 | Sikkenga et al. | 562/413 |
| 5,304,676 | 4/1994 | Hindmarsh et al. | 562/414 |
| 5,306,845 | 4/1994 | Yokohama et al. | 568/484 |
| 5,344,969 | 9/1994 | Iwane et al. | 562/486 |
| 5,354,898 | 10/1994 | Schroeder | 562/485 |
| 5,362,908 | 11/1994 | Schroeder et al. | 562/487 |
| 5,563,293 | 10/1996 | Hindmarsh et al. | 562/414 |
| 5,567,842 | 10/1996 | Izumisawa et al. | 562/486 |

METHOD TO REDUCE CARBOXYBENZALDEHYDE ISOMERS IN TEREPHTHALIC ACID OR ISOPHTHALIC ACID

This application is a continuation-in-part of co-pending application Ser. No. 09/074,251, filed May 7, 1998, entitled Method and Apparatus for Preparing Purified Terephthalic Acid, which is a divisional of 08/477,898, filed Jun. 7, 1995, entitled Method and Apparatus for Preparing Purified Terephthalic Acid, now U.S. Pat. No. 5,767,311, and is also a continuation-in-part of application Ser. No. 08/962,030, filed Oct. 31, 1997, entitled Method and Apparatus for Preparing Purified Terephthalic Acid, which is a continuation-in-part of application Ser. No. 08/760,890, filed Dec. 6, 1996, entitled Method and Apparatus for Preparing Purified Terephthalic Acid, which is in turn a continuation-in-part of application Ser. No. 08/477,898, filed Jun. 7, 1995, entitled Method and Apparatus for Preparing Purified Terephthalic Acid, now U.S. Pat. No. 5,767, 311, all four of which are assigned to the same assignee as this application, and the totality of the disclosures of which are hereby incorporated herein by reference for all purposes.

FIELD OF INVENTION

The present invention relates to methods for reducing 4-carboxybenzaldehyde (4-CBA) and 3-carboxybenzaldehyde (3-CBA) and, more specifically, to a method for reduction of 4-CBA in crude terephthalic acid (TPA) or 3-carboxybenzaldehyde (3-CBA) in crude isophthalic acid (IPA).

BACKGROUND OF THE INVENTION

Recent advances in terephthalic acid (TPA) manufacturing processes require relatively high p-xylene purity (99.7+%) in order to improve the quality of the product and reduce the costs of manufacturing. This is because such processes use hydrogenation as the main method for purifying the crude terephthalic acid produced in the oxidation section of the processes. Although the hydrogenation method is very selective for elimination of the major impurity, 4-carboxybenzaldehyde (4-CBA), by converting it to p-toluic acid, such methods can tolerate only very small amounts of 4-CBA (preferably less than 3,000 ppm).

The small amount of 4-CBA (or 3-CBA in isophthalic acid (IPA) production) can not be oxidized to TPA (or IPA) in the oxidizer, because the solvent used in the oxidizer, acetic acid, is a poor solvent to significantly dissolve TPA (or IPA) and 4-CBA (or 3-CBA). In fact, in traditional processes almost all the TPA (or IPA) and 4-CBA (or 3-CBA) produced are precipitated in the oxidizer to form a slurry. Therefore, a small amount of 4-CBA (or 3-CBA) is encapsulated inside of the TPA (or IPA) solids, and can not be further oxidized by air to form TPA (or IPA) in the oxidizer. It should be noted that even though the 4-CBA (or 3-CBA) is an aldehyde which can easily be oxidized to TPA (or IPA) by air under the oxidizer operating conditions, since it is present as a solid, it is not readily oxidized. Thus, there remains a need for a method for reduction of 4-CBA or 3-CBA from crude TPA or crude IPA, respectively, without encountering the disadvantages outlined above.

SUMMARY OF THE INVENTION

In accordance with the present invention there is provided a method for reducing carboxybenzaldehyde isomers (4-CBA or 3-CBA) from crude TPA/IPA, whereby crude TPA or crude IPA is dissolved in N-methyl pyrrolidone (NMP) and is then contacted with substantially anhydrous hydrogen peroxide (containing an optimized amount of water) or with air to convert 4-CBA to TPA (or 3-CBA to IPA) at a conversion rate of 40% to 50% per pass, under moderate temperature and pressure.

An important aspect of the present invention is related to the development of proprietary solvents which can completely dissolve both TPA (or IPA) and 4-CBA (or 3-CBA) in the crude TPA (or IPA) solids produced by the oxidizer. Another aspect of the invention is related to the development of the methods and conditions to react the dissolved 4-CBA (or 3-CBA) with oxidants, such as hydrogen peroxide, pure oxygen, air, or other oxidants, in a manner where the oxidant has minimum adverse effects on the solvent in the solution. Using the present invention, major impurities (e.g., 4-CBA or 3-CBA) can be oxidized to desired products (e.g., TPA or IPA) which in turn can be recovered within the process, thereby increasing p-xylene (or m-xylene) yields.

Characteristics of CBA oxidants useful in the present invention include oxidants: (a) in which no additional impurities or by-products are introduced to the process other than water; (b) which can be concentrated in stable form in the preferred solvent such as N-methyl pyrrolidone (NMP) (or methanol for IPA purification); (c) with which relatively high conversion of CBA can be obtained with a low molar ratio of oxidant/CBA; and (d) with which the product of oxidation should be substantially TPA (or IPA) with water as a byproduct. It is to be understood that the term "CBA oxidants" is intended for purposes of this application to encompass all oxidants which are useful in the oxidation of 4-CBA and 3-CBA to TPA and IPA, respectively, as described herein.

In accordance with the invention, one of the preferred CBA oxidants is substantially anhydrous hydrogen peroxide concentrated in a preferred solvent with a small amount of water added. This CBA oxidant is preferred for oxidation of minor amounts of 4-CBA (or 3-CBA) contained in solution. Anhydrous hydrogen peroxide is highly reactive, commercially available, and degradation products are environmentally benign. Hydrogen peroxide can be concentrated in stable form in NMP (one of the preferred solvents for CBA oxidation).

In accordance with the invention, another preferred CBA oxidant is air (or pure oxygen) for oxidation of minor amount of a 4-CBA (or 3-CBA) contained in the solution.

Although substantially anhydrous hydrogen peroxide and air (or pure oxygen) are preferred CBA oxidants, it is to be understood that, in accordance with the invention, the CBA oxidants useful for conversion of CBA isomers in conjunction with the present invention can be selected from various oxidants which are capable of oxidizing aldehydes in solutions, including, without limitation, hydrogen peroxide in water, ozone, carbon tetrachloride, trichloroacetaldehyde, hexamine, acetone, cyclohexanone, benzophenone, cinnamaldehyde, dimethyl sulfoxide, sulfides, chiral oxidants, glyoxals and organic peroxy acids, which include performic acid, peracetic acid, perbenzoic acid, perpropionic acid, permaleic acid, and perphthalic acid.

BRIEF DESCRIPTION OF THE DRAWINGS

A more complete understanding of the methods of the present invention may be obtained by reference to the following Detailed Description when taken in conjunction with the accompanying Drawings wherein.

DETAILED DESCRIPTION OF EMBODIMENTS

The present invention relates to the a method for reducing carboxybenzaldehyde isomers from crude TPA or IPA. For illustration purposes, an embodiment of the method of the present invention will be discussed in connection with a recently developed process for the production of TPA and IPA from mixed xylenes.

Figure 1:
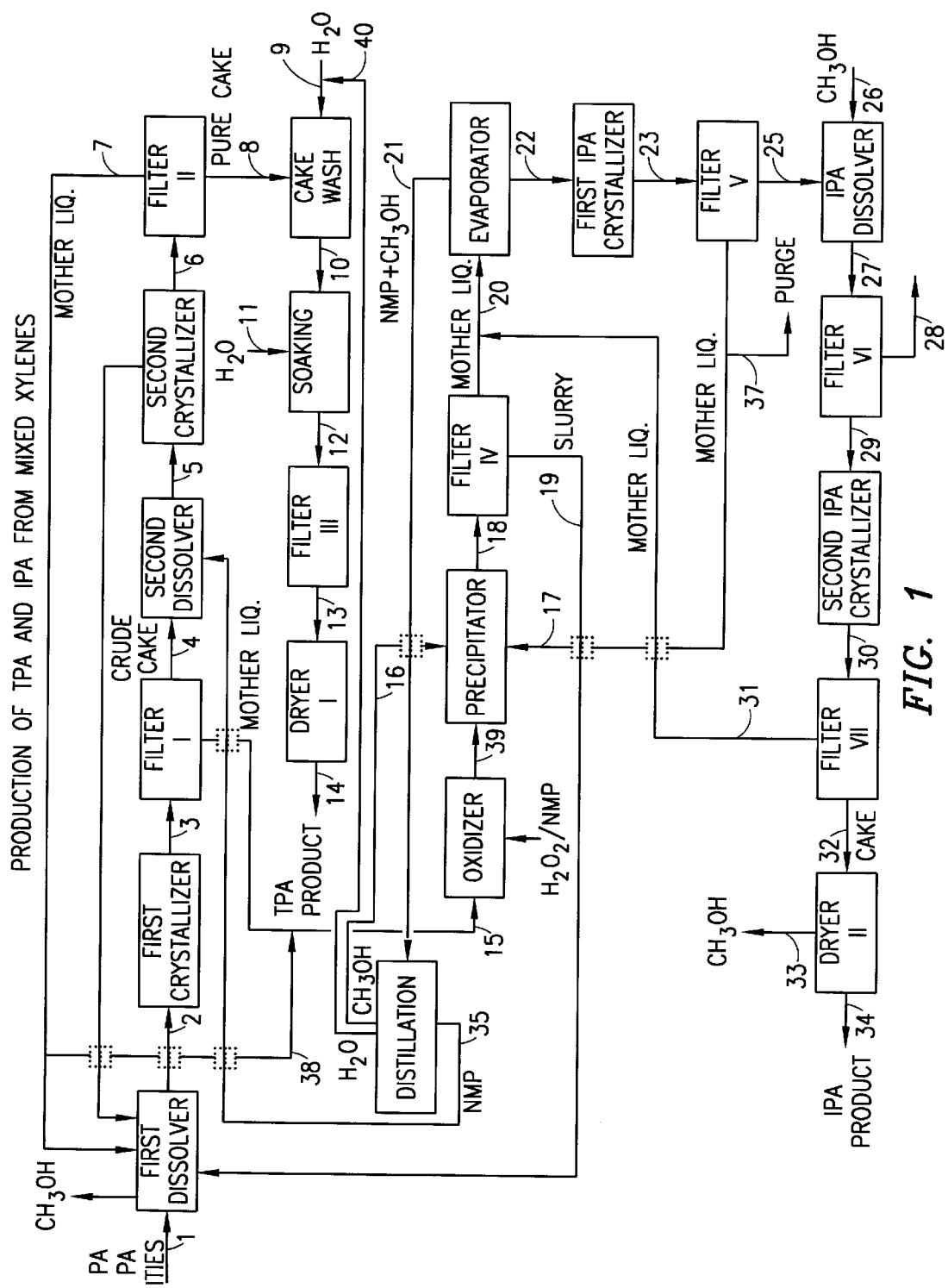
FIG. 1 is a schematic representation of a method of production of TPA and IPA from mixed xylenes.

Now referring to FIG. 1, there is illustrated a schematic representation of a new method for the production of TPA and IPA from mixed xylenes. This new method is more fully detailed in co-pending application Ser. No. 09/097,930, filed Jun. 16, 1998, also assigned to the assignee of the invention described herein, the totality of the subject matter thereof being incorporated herein by reference for all purposes.

In FIG. 1, crude TPA from the oxidation section (containing mainly TPA and minor amounts of 4-CBA and p-toluic acid) is fed to Dissolver I through Line 1 to mix with the mother liquor from Filter II (through Line 7) and the slurry from Filter IV (through Line 26). The temperature in the Dissolver I is maintained at 160° C. to 180° C. so as to completely dissolve the solids.

The saturated solution from the Dissolver I is then fed continuously to a first cooling crystallizer (Crystallizer I) via Line 2 to generate TPA salt crystals at 30° C. to 50° C. The slurry containing said TPA salt crystals exits the Crystallizer I through Line to a Filter I where the crude cake is removed and fed to the Dissolver II through Line 4. In the Dissolver II the cake is re-dissolved in clean NMP recycled through Line 20 from NMP/water distillation column (Distillation). Again, the temperature in the Dissolver II is kept at 160° C. to 180° C. to completely dissolve the TPA salt crystals. The saturated solution from the Dissolver II is continuously fed through Line 5 to a Crystallizer II where the temperature is maintained at a minimum of 60° C. to prevent the formation of salt TPA crystals. The degree of temperature reduction in the Crystallizer II is controlled by the amount of NMP flashed through the Crystallizer II via pressure reduction. The flashed NMP is recycled to the Dissolver I through Line 27.

The slurry from the Crystallizer II is fed to a Filter II through Line 6 where the purified TPA solid cake is recovered and sent to a Cake Wash via Line 8, while the mother liquor is recycled to Dissolver I via Line 7. In the Cake Wash, the bulk residual NMP in the cake is removed via counter-current washing techniques using water and, thereafter, the washed cake is fed through Line 10 to a soaker (Water Crystallizer) for removal of any trace NMP in the TPA cake via washing with water at temperatures of between 160° C. and 280° C. The NMP-free TPA cake is then provided via Line 12 to Filter III where it is filtered before being provided via Line 14 to Dryer I for drying to yield the final TPA product.

The mother liquor from Filter I (containing solvent (e.g. NMP), TPA, 4-CBA, p-toluic acid and other minor impurities) is transferred via Line 15 to a CBA Oxidizer to react hydrogen peroxide in NMP (with a proper amount of water). The CBA Oxidizer is preferably operated at 25° C. to 50° C. and under pressure of between about 1 atmosphere and about 5 atmospheres. Approximately 40%–60% of the 4-CBA in the mother liquor from Filter I is converted to TPA via the process described above. The effluent from the CBA Oxidizer is transferred to the Evaporator via Line 16 to evaporate off NMP and water from the mixture. The resulting concentrated solution is removed from the bottom of the Evaporator and is provide via Line 19 to a Crystallizer III. In the Crystallizer III, solids recovery is maximized by operating the Crystallizer II at a temperature of between 0° C. and 60° C. and under pressure. The slurry produced from the Crystallizer III is subsequently transferred through Line 23 to Filter IV, where the cake is recycled to the Dissolver I via Line 26 and a major portion of the mother liquor is recycled to the Evaporator via Line 24. A small remaining portion of the mother liquor is purged via Line 25.

The NMP and water mixture from the Evaporator is provided to a distillation column (Distillation) via Line 18, where water is recovered as the overhead stream and sent to the Cake Wash via Line 21. Solvent (e.g., NMP) is recovered as a bottom product of the Distillation and recycled to the Dissolver II via Line 20.

The following examples illustrate the effectiveness of the CBA oxidant in converting 4-CBA to TPA in an organic solution such as NMP, which is the principle and feature of this invention.

EXAMPLE 1

This example describes the reduction of 4-CBA to TPA in the presence of hydrogen peroxide as determined by gas chromatography using the process of the present invention. A solution of 4-CBA in NMP was prepared. This solution was heated to 120° C. for approximately 6 hours. The solution was then divided into four 30 ml samples. To one sample, commercially available 30 wt % hydrogen peroxide was added as an oxidizing agent. The other three samples were heated for an additional 2 hours at 120° C. before oxidizing agents were added to two of the samples. The oxidants used were 30 wt % hydrogen peroxide and potassium permanganate ($KMnO_4$). After the addition of the oxidants, the samples were heated for an additional two hours. Those containing hydrogen peroxide were heated at 100° C., while the one containing $KMnO_4$ was kept at 120° C. Table 1 presents a summary of these results. As can be seen, the hydrogen peroxide is effective at oxidizing 4-CBA to TPA (samples 1B and 2). The other strong oxidizing agent, potassium permanganate, (sample 1C), did not oxidize the 4-CBA to TPA. The control (sample 1A) also showed no oxidation of 4-CBA to TPA.

TABLE 1

| Sample | Initial treatment conditions | Oxidant | Oxidizing conditions | 4-CBA (ppm) | TPA (ppm) | Benzoic Acid (ppm) | p-Toluic Acid (ppm) |
|---|---|---|---|---|---|---|---|
| Feed | 6 hr @ 120° C. | — | | 81,775 | 0 | 0 | 1,625 |

TABLE 1-continued

| Sample | Initial treatment conditions | Oxidant | Oxidizing conditions | 4-CBA (ppm) | TPA (ppm) | Benzoic Acid (ppm) | p-Toluic Acid (ppm) |
|---|---|---|---|---|---|---|---|
| 1A | 8 hr @ 120° C. | — | | 76,025 | 0 | 2 | 1,550 |
| 1B | 8 hr @ 120° C. | $H_2O_2$ | 4 hr @ 100° C. | 46,500 | 64,800 | 2 | 1,450 |
| 1C | 8 hr @ 120° C. | $KMnO_4$ | 4 hr @ 120° C. | 74,450 | 0 | 2 | 13 |
| 2 | 6 hr @ 120° C. | $H_2O_2$ | 2 hr @ 100° C. | 48,050 | 68,225 | 240 | 1,500 |

EXAMPLE 2

Example 2 illustrates the effect of reaction time on the amount of TPA produced from 4-CBA within the process of the present invention. The oxidation occurs rapidly as no significant change can be seen in the concentration of 4-CBA after the first minute of reaction. This example also indicates that reaction temperature has little effect on the reaction rate. In this experiment, the feed solution was divided into equal portions, each weighing approximately 25 grams. These samples were heated to the temperature shown in the tables below using an oil bath. One sample from each test was designated as a control with no oxidant addition. A solution of anhydrous hydrogen peroxide was prepared by adding commercially available 30 wt % hydrogen peroxide in water to NMP and distilling off the water, resulting in a virtually anhydrous hydrogen peroxide solution stabilized in NMP. A designated amount of anhydrous hydrogen peroxide was added to the remaining samples. A solution of 40 wt % sodium thiosulfate (STS) was prepared in HPLC water. After a specified reaction period, STS was added in excess to quench the oxidation reaction. Each sample was removed from the oil bath and cooled to room temperature (where applicable). The samples were then filtered and the filtrate analyzed by gas chromatography. The results are shown in Tables 2 through 5.

TABLE 2

| Sample | Reaction Temperature (° C.) | Molar Ratio $H_2O_2$/4-CBA | Molar Ratio STS/$H_2O_2$ | Reaction Time (Min). | Final 4-CBA Concentration (ppm) |
|---|---|---|---|---|---|
| 2a | 90 | 0 | — | control | 4800 |
| 2b | 90 | 4.81 | 3.8 | 0.08 | 4100 |
| 2c | 90 | 5.17 | 3.5 | 1 | 3350 |
| 2d | 90 | 5.75 | 3.5 | 5 | 3100 |
| 2e | 90 | 6.49 | 3.5 | 15 | 3225 |
| 2f | 90 | 5.36 | 3.6 | 30 | 3300 |
| 2g | 90 | 5.44 | 3.5 | 60 | 3250 |

TABLE 3

| Sample | Reaction Temperature (° C.) | Molar Ratio $H_2O_2$/4-CBA | Molar Ratio STS/$H_2O_2$ | Reaction Time (min) | Final 4-CBA Concentration (ppm) |
|---|---|---|---|---|---|
| 3a | 23 | 0 | — | control | 4150 |
| 3b | 23 | 6.29 | 3.5 | 0.08 | 2575 |
| 3c | 23 | 6.19 | 3.5 | 1 | 3050 |
| 3d | 23 | 5.49 | 3.6 | 5 | 2800 |
| 3e | 23 | 6.03 | 3.6 | 15 | 2875 |
| 3f | 23 | 7.76 | 3.6 | 30 | 2625 |
| 3g | 23 | 4.98 | 3.6 | 60 | 2975 |

TABLE 4

| Sample | Reaction Temp (° C.) | Molar Ratio $H_2O_2$/4-CBA | Molar Ratio STS/$H_2O_2$ | STS Added | Reaction Time (Min) | Final 4-CBA Concentration (ppm) |
|---|---|---|---|---|---|---|
| 4a | 90 | 0 | — | No | control | 4175 |
| 4b | 90 | 4.43 | 4.9 | Yes | 1 | 3700 |
| 4c | 90 | 0 | — | Yes | — | 4375 |

TABLE 5

| Sample | Reaction Temp (° C.) | Molar Ratio $H_2O_2$/4-CBA | Molar Ratio STS/$H_2O_2$ | STS Added | Reaction Time (Min) | Final 4-CBA Concentration (ppm) |
|---|---|---|---|---|---|---|
| 5a | 90 | 0 | — | No | control | 9400 |
| 5b | 90 | 2.59 | 3.8 | Yes | 1 | 7425 |
| 5c | 90 | 0 | — | Yes | — | 9225 |

EXAMPLE 3

Example 3 illustrates the effect of the relative amount of hydrogen peroxide to 4-CBA on the conversion of 4-CBA to TPA using the present invention process. This example also illustrates the necessity of having a small amount of water present to aid in the oxidation reaction. Two solutions of 4-CBA and TPA in NMP were prepared and heated at 165° C. for approximately 10 minutes to ensure complete dissolution. The concentration of TPA in these solutions was four times the concentration of 4-CBA. The solutions were cooled to 23° C., and separated into samples. Varying amounts of water and anhydrous hydrogen peroxide in NMP were added to each sample. A control sample, to which no water or hydrogen peroxide was added, was included. The samples were then analyzed by gas chromatography for 4-CBA. Analytical results were compensated to eliminate the effects of dilution. Table 6 summarizes the results. It is evident from Sample 1, 3 and 13 that for a given mole ratio of $H_2O_2$/4-CBA, the presence of water significantly increased the conversion of 4-CBA to TPA.

TABLE 6

| Sample | Feed 4-CBA conc. (ppm) | Mole ratio $H_2O$/4-CBA | Mole ratio $H_2O_2$/4-CBA | Product 4-CBA conc. (ppm) | Conversion (% 4-CBA reacted) |
|---|---|---|---|---|---|
| 1  | 5,061 | 0    | 10.92 | 4,403 | 13 |
| 2  | 5,061 | 1.13 | 11.16 | 2,713 | 46 |
| 3  | 5,061 | 0.62 | 10.69 | 1,878 | 63 |
| 4  | 5,061 | 0    | 0     | 5,061 | 0  |
| 5  | 9,890 | 0.99 | 5.48  | 5,654 | 43 |
| 6  | 9,890 | 0.51 | 5.39  | 5,871 | 41 |
| 7  | 9,890 | 0.23 | 5.39  | 5,860 | 41 |
| 8  | 9,890 | 0.09 | 5.38  | 5,377 | 45 |
| 9  | 9,890 | 2.01 | 5.56  | 5,547 | 44 |
| 10 | 9,890 | 4.83 | 5.76  | 5,412 | 45 |
| 11 | 9,890 | 0.47 | 1.06  | 7,983 | 19 |
| 12 | 9,890 | 0.48 | 2.53  | 7,775 | 21 |
| 13 | 9,890 | 0.51 | 10.42 | 4,352 | 56 |

Although preferred embodiments of the method of the present invention have been illustrated in the accompanying Drawings and Tables and described in the foregoing Detailed Description, it will be understood that the invention is not limited to the embodiments disclosed, but is capable of numerous rearrangements, modifications and substitutions without departing from the spirit of the invention as set forth and defined by the following claims.

What is claimed is:

1. A method for reducing 4-carboxybenzaldehyde (4-CBA) in terephthalic acid (TPA) production or 3-carboxybenzaldehyde (3-CBA) in isophthalic acid production comprising:

(a) dissolving the crude TPA (or crude IPA) in a solvent at a temperature of from about 50° C. to about 250° C. to form a solution;

(b) crystallizing purified acid from said solution by reducing the temperature and/or pressure thereof;

(c) separating said crystallized purified TPA from said solution;

(d) adding an oxidant to CBA oxidizer to oxidize said filtered solution in (c) causing 4-CBA (or 3-CBA) to convert to TPA (or IPA);

(e) evaporating the solvent from the said solution from (d);

(f) cooling the concentrated solution from (e) to crystallize additional purified TPA and filtering the said slurry; and recycling the major portion of the mother liquor from (f) to dissolver in (a) and a minor portion of the mother liquor from (f) to a purge stream.

2. A method in accordance with claim 1 said oxidant is selected the group consists of anhydrous hydrogen peroxide in organic solvents, air, enriched air, pure oxygen, hydrogen peroxide in water, ozone, carbon tetrachloride, trichloroacetaldehyde, hexamine, acetone, cyclohexanone, benzophenone, cinnamaldehyde, dimethyl sulfoxide, sulfides, chiral oxidants, glyoxals, organic peroxy acids, such as performic acid, peracetic acid, perbenzoic acid, perpropionic acid, permaleic acid, and perphthalic acid.

3. A method in accordance with claim 2 in which said 4-CBA (or 3-CBA) oxidant consists of hydrogen peroxide with 0 to 5 wt % water stabilized in NMP.

4. A method in accordance with claim 2 in which said 4-CBA (or 3-CBA) oxidant is air.

5. A method in accordance with claim 1 in which said dispersion (crude TPA) contains at least 80 to 99+% terephthalic acid (TPA), 0 to 20% isophthalic acid (IPA), and minor amounts of 4-carboxyaldehyde (4-CBA), 3-carboxyaldehyde (3-CBA) and impurities selected from unreacted starting materials, solvents, products of side reactions and/or other undesired materials.

6. A method in accordance with claim 1 in which said dispersion (crude IPA) contains 95+% IPA, 0 to 5% 3-CBA, and minor amounts of impurities selected from unreacted starting materials, solvents, products of side reactions and/or other undesired materials.

7. A method in accordance with claim 1 wherein said solvent for dissolving crude TPA (or IPA) is selected from the group consisting of N-methyl pyrrolidone (NMP), N,N-dimethyl acetamide, N,N-dimethyl formamide, N-formyl piperidine, N-alkyl-2-pyrrolidone (including N-ethyl pyrrolidone), N-mercaptoalkyl-2-pyrrolidone (including N-mercaptoethyl-2-pyrrolidone), N-alkyl-2-thiopyrrolidone (including N-methyl-2-thiopyrrolidone), N-hydroxyalkyl-2-pyrrolidone (including N-hydroxyethyl-2-pyrrolidone), the morpholines (including morpholine, and N-formyl morpholine), the carbitols, $C_1$ to $C_{12}$ alcohols, the ethers, the amines, the amides, and the esters, and mixtures thereof.

8. A method in accordance with claim 7 wherein said solvent for TPA is N-methyl pyrrolidone or N,N-dimethyl acetamide.

9. A method in accordance with claim 8 wherein said selective crystallization solvent for TPA purification is N-methyl pyrrolidone.

10. A method in accordance with claim 7 wherein said solvent for IPA is N-methyl pyrrolidone, N,N-dimethyl acetamide, or methanol.

11. A method in accordance with claim 10 wherein said solvent for IPA is N-methyl pyrrolidone.

12. A method in accordance with claim 1 wherein said crude CBA oxidizer is operated at 0° C. to 150° C. under 1 atm to 20 atm pressure.

13. A method in accordance with claim 1 wherein said CBA oxidizer is operated at a hydrogen peroxide-to-CBA mole ratio of 0.5 to 15.

14. A method in accordance with claim 1 wherein said CBA oxidizer is operated at a water-to-CBA mole ratio of 0 to 5, using hydrogen peroxide stabilized in NMP as the oxidant.

15. A method in accordance with claim 1 wherein said CBA oxidizer is operated at an air-to-CBA mole ratio of 1 to 100, using air as the oxidant.

16. A method in accordance with claim 1 wherein the reaction residence time in said CBA oxidizer is 0.1 minute to 6 hours.

17. A method in accordance with claim 1 wherein said crude CBA oxidizer is operated at 20° C. to 100° C. under 1 atm to 5 atm pressure.

18. A method in accordance with claim 1 wherein said CBA oxidizer is operated at a hydrogen peroxide- to-CBA mole ratio of 2 to 5.

19. A method in accordance with claim 1 wherein said CBA oxidizer is operated at a water-to-CBA mole ratio of 1 to 5, using hydrogen peroxide stabilize in NMP as the oxidant.

20. A method in accordance with claim 1 wherein said CBA oxidizer is operated at an air-to-CBA mole ratio of 1 to 20, using air as the oxidant.

21. A method in accordance with claim 1 wherein the reaction residence time in said CBA oxidizer is 1 minute to 5 minutes.

22. A method for reducing 4-carboxybenzaldehyde (4-CBA) in terephthalic acid (TPA) production or 3-carboxybenzaldehyde (3-CBA) in isophthalic acid production comprising:
(a) dissolving the crude TPA (or crude IPA) in a solvent at a temperature of from about 50° C. to about 250° C. to form a solution;
(b) adding an oxidant to the said solution in (a) to convert a significant portion of 4-CBA (or 3-CBA) to TPA (or IPA);
(c) crystallizing purified TPA (or IPA) from said solution by reducing the temperature and/or pressure thereof;
(d) separating said crystallized purified TPA (or IPA) from said solution;
(e) evaporating the solvent from the said mother liquor from (d);
(f) cooling the said concentrated solution from (e) to crystallize additional purified TPA (or IPA);
(g) separating the said crystallized TPA (or IPA) from (f); and
recycling the major portion of the mother liquor from (g) to (a) and sending a minor portion of the mother liquor from (g) to a purge stream.

23. A method in accordance with claim 22 said oxidant is selected the group consists of anhydrous hydrogen peroxide in organic solvents, air, enriched air, pure oxygen, hydrogen peroxide in water, ozone, carbon tetrachloride, trichloroacetaldehyde, hexamine, acetone, cyclohexanone, benzophenone, cinnamaldehyde, dimethyl sulfoxide, sulfides, chiral oxidants, glyoxals, organic peroxy acids, such as performic acid, peracetic acid, perbenzoic acid, perpropionic acid, permaleic acid, and perphthalic acid.

24. A method in accordance with claim 23 in which said 4-CBA (or 3-CBA) oxidant consists of hydrogen peroxide with 0 to 5 wt % water stabilized in NMP.

25. A method in accordance with claim 23 in which said 4-CBA (or 3-CBA) oxidant is air.

26. A method in accordance with claim 22 in which said dispersion (crude TPA) contains at least 80 to 99+% terephthalic acid (TPA), 0 to 20% isophthalic acid (IPA), and minor amounts of 4-carboxyaldehyde (4-CBA), 3-carboxyaldehyde (3-CBA) and impurities selected from unreacted starting materials, solvents, products of side reactions and/or other undesired materials.

27. A method in accordance with claim 22 in which said dispersion (crude IPA) contains 95+% IPA, 0 to 5% 3-CBA, and minor amounts of impurities selected from unreacted starting materials, solvents, products of side reactions and/or other undesired materials.

28. A method in accordance with claim 22 wherein said solvent for dissolving crude TPA (or IPA) is selected from the group consisting of N-methyl pyrrolidone (NMP), N,N-dimethyl acetamide, N,N-dimethyl formamide, N-formyl piperidine, N-alkyl-2-pyrrolidone (including N-ethyl pyrrolidone), N-mercaptoalkyl-2-pyrrolidone (including N-mercaptoethyl-2-pyrrolidone), N-alkyl-2-thiopyrrolidone (including N-methyl-2-thiopyrrolidone), N-hydroxyalkyl-2-pyrrolidone (including N-hydroxyethyl-2-pyrrolidone), the morpholines (including morpholine, and N-formyl morpholine), the carbitols, $C_1$ to $C_{12}$ alcohols, the ethers, the amines, the amides, and the esters, and mixtures thereof.

29. A method in accordance with claim 28 wherein said solvent for TPA is N-methyl pyrrolidone or N,N-dimethyl acetamide.

30. A method in accordance with claim 29 wherein said selective crystallization solvent for TPA purification is N-methyl pyrrolidone.

31. A method in accordance with claim 28 wherein said solvent for IPA is N-methyl pyrrolidone, N,N-dimethyl acetamide, or methanol.

32. A method in accordance with claim 31 wherein said solvent for IPA is N-methyl pyrrolidone.

33. A method in accordance with claim 22 wherein said crude TPA (or IPA) dissolver also serves as CBA oxidizer and is operated at 50° C. to 250° C. under 1 atm to 20 atm pressure.

34. A method in accordance with claim 22 wherein said crude TPA (or IPA) dissolver also serves as CBA oxidizer and is operated at a hydrogen peroxide- to-CBA mole ratio of 0.5 to 15.

35. A method in accordance with claim 22 wherein said crude TPA (or IPA) dissolver also serves as CBA oxidizer and is operated at a water-to-CBA mole ratio of 0 to 5, using hydrogen peroxide stabilized in NMP as the oxidant.

36. A method in accordance with claim 22 wherein said crude TPA (or IPA) dissolver also serves as CBA oxidizer and is operated at an air-to-CBA mole ratio of 1 to 100, using air as the oxidant.

37. A method in accordance with claim 22 wherein the reaction residence time of oxidant in said crude TPA (or IPA) dissolver which also serves as CBA oxidizer is 0.1 minute to 6 hours.

38. A method in accordance with claim 22 wherein said crude TPA (or IPA) dissolver also serves as CBA oxidizer and is operated at 100° C. to 180° C. under 1 atm to 5 atm pressure.

39. A method in accordance with claim 22 wherein said crude TPA (or IPA) dissolver also serves as CBA oxidizer and is operated at a hydrogen peroxide- to-CBA mole ratio 2 to 5.

40. A method in accordance with claim 22 wherein said crude TPA (or IPA) dissolver also serves as CBA oxidizer and is operated at a water-to-CBA mole ratio of 1 to 5, using hydrogen peroxide stabilized in NMP as the oxidant.

41. A method in accordance with claim 22 wherein said crude TPA (or IPA) dissolver also serves as CBA oxidizer and is operated at an air-to-CBA mole ratio of 1 to 20, using air as the oxidant.

42. A method in accordance with claim 22 wherein the reaction residence time of oxidant in said crude TPA (or IPA) dissolver which also serves as CBA oxidizer is 1 minute to 5 minutes.

* * * * *

UNITED STATES PATENT AND TRADEMARK OFFICE
CERTIFICATE OF CORRECTION

PATENT NO. :   5,929,274
DATED      :   Jul. 27, 1999
INVENTOR(S) :  Lamshing et al.

It is certified that error appears in the above-identified patent and that said Letters Patent is hereby corrected as shown below:

Column 2, line 45     Before "minor"
                          Insert --a--

Column 2, line 46     After "of"
                          Remove --a--

Column 9, line 27     Replace "stabilize"
                          With --stabilized--

Signed and Sealed this

Twenty-seventh Day of June, 2000

Attest:

Q. TODD DICKINSON

Attesting Officer                Director of Patents and Trademarks

UNITED STATES PATENT AND TRADEMARK OFFICE
CERTIFICATE OF CORRECTION

PATENT NO.    : 5,929,274
DATED         : July 27, 1999
INVENTOR(S)   : Lamshing, et al.

Figure 2:
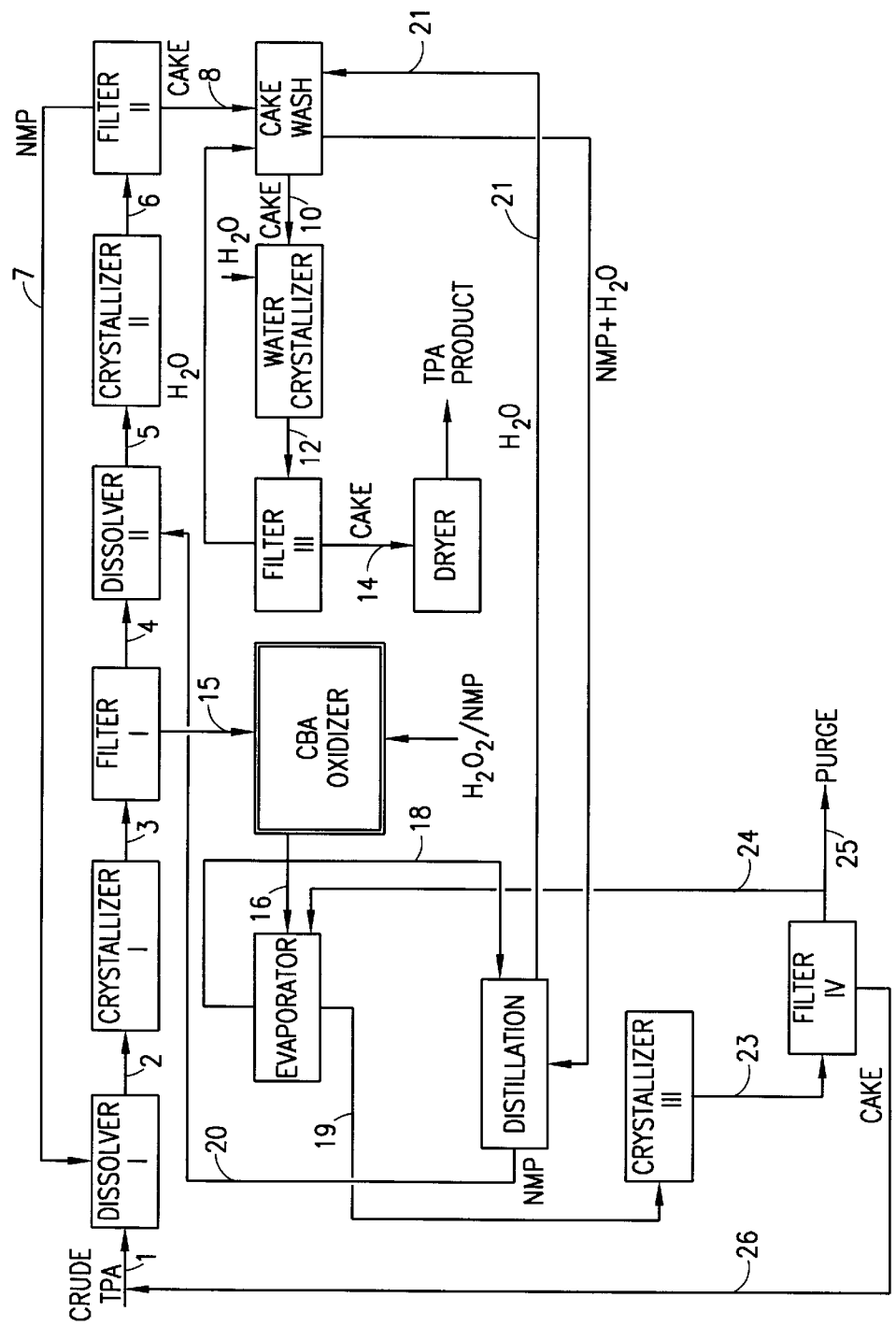
FIG. 2 is a schematic representation of an embodiment of the improved carboxybenzaldehyde isomers reduction method of the present invention.

It is certified that error appears in the above-identified patent and that said Letters Patent is hereby corrected as shown below:

Column 3,
Line 20, replace "FIG. 1" with -- FIGS. 1 and 2, and more specifically in FIG. 2 --
Line 17, after "1998", add -- now issued as U.S. Patent No. 6,054,610 --
Lines 43-44 replace "through Line 27" with -- through a Line (not shown) --

Signed and Sealed this

Ninth Day of October, 2001

*Attest:*

*Attesting Officer*

NICHOLAS P. GODICI
*Acting Director of the United States Patent and Trademark Office*